(12) United States Patent
Shaw

(10) Patent No.: US 7,503,919 B2
(45) Date of Patent: Mar. 17, 2009

(54) LOCKING COMPRESSION HIP SCREW

(76) Inventor: James Albert Shaw, 7817 Tomlinson Ave., Cabin John, MD (US) 20818

( * ) Notice: Subject to any disclaimer, the term of this patent is extended or adjusted under 35 U.S.C. 154(b) by 382 days.

(21) Appl. No.: 11/413,672

(22) Filed: Apr. 28, 2006

(65) Prior Publication Data

US 2007/0270847 A1 Nov. 22, 2007

(51) Int. Cl.
*A61B 17/58* (2006.01)
(52) U.S. Cl. ...................................... 606/65
(58) Field of Classification Search ............. 606/60, 606/65, 66, 67, 68
See application file for complete search history.

(56) References Cited

U.S. PATENT DOCUMENTS

| | | | | |
|---|---|---|---|---|
| 2,628,614 | A * | 2/1953 | Briggs | 606/67 |
| 2,702,543 | A * | 2/1955 | Pugh et al. | 606/67 |
| 3,374,786 | A * | 3/1968 | Callender, Jr. | 606/65 |
| 4,432,358 | A * | 2/1984 | Fixel | 606/66 |
| 4,612,920 | A * | 9/1986 | Lower | 606/66 |
| 4,617,922 | A * | 10/1986 | Griggs | 606/66 |
| 4,621,629 | A * | 11/1986 | Koeneman | 606/65 |
| 4,628,923 | A * | 12/1986 | Medoff | 606/65 |
| 4,657,001 | A * | 4/1987 | Fixel | 606/66 |
| 5,007,910 | A * | 4/1991 | Anapliotis et al. | 606/65 |
| 5,032,125 | A * | 7/1991 | Durham et al. | 606/62 |
| 5,041,116 | A * | 8/1991 | Wilson | 606/65 |
| 5,167,663 | A * | 12/1992 | Brumfield | 606/64 |
| 5,324,292 | A * | 6/1994 | Meyers | 606/66 |
| 5,454,813 | A * | 10/1995 | Lawes | 606/62 |
| 5,514,138 | A * | 5/1996 | McCarthy | 606/65 |
| 5,743,912 | A * | 4/1998 | Lahille et al. | 606/65 |
| 6,443,954 | B1 * | 9/2002 | Bramlet et al. | 606/62 |
| 6,645,209 | B2 * | 11/2003 | Hall, IV et al. | 606/281 |
| 2002/0049445 | A1 * | 4/2002 | Hall et al. | 606/69 |
| 2005/0010224 | A1 * | 1/2005 | Watkins et al. | 606/65 |

OTHER PUBLICATIONS

Cole, Peter A and Bhandari, Mohit Specialty Update & What's New in Orthopaedic Trauma Journal of Bone and Joint Surgery Dec. 2005; p. 2823-2838; vol. 87-A No. 12 The Journal of Bone and Joint Surgery; Needham MA.
Palm, Henrik; Jacobsen, Steffen; Sonne-Holm, STK and Gebuhr, Peter Integrity of the Lateral Femoral Wail in Intertromauteric Hipfractures & An Important Pedictor of a Reoperation The Journal of Bone and Joint Surgery Mar. 2007; p. 470-475; vol. 89-A No. 3 The Journal of Bone and Joint Surgery, Inc Needham, MA.
Shaw, James A and Wilson, Scott Internal Fixation of Proximal Femur Fractures: A Biomechanical Comparison of the Gamma Locking Nail and the Omega Compression Hip Screen Orthopedic Review Jan. 1993 p. 61-68 vol. 22 No. 1 The American Journal of Orthopedics/Quadrant HealthCom, Inc. Parsippany, NJ.

* cited by examiner

*Primary Examiner*—Eduardo C Robert
*Assistant Examiner*—Julianna N Harvey

(57) ABSTRACT

A reverse obliquity fracture of the proximal femur is poorly secured with current generation hip screws, frequently necessitating the use of intramedullary fracture fixation devices or external fixation hardware. This compression hip screw comprises a femoral head lag screw, side plate, locking plug, and compressing screw, which can be assembled in a locked mode, preventing lateral translation of the lag screw within the side plate. In the locked mode, the proximal fracture fragment(s) are prevented from displacing laterally relative to the distal fragment, as occurs commonly when such a fracture is fixed with a conventional hip screw. No change in routine fracture reduction or insertion technique is required to use this compression hip screw. Additionally, this compression hip screw can be used in a dynamic or sliding mode, if so desired, when used to fix the more common femoral neck or intertrochanteric fracture patterns.

1 Claim, 3 Drawing Sheets

LOCKING COMPRESSION HIP SCREW

CROSS REFERENCE TO RELATED APPLICATIONS

Not Applicable

FEDERALLY SPONCERED RESEARCH AND DEVELOPEMENT

Not Applicable

REFERENCES CITED [REFERENCED BY]

| U.S. Patent Document | | | |
|---|---|---|---|
| 4,432,358 | February 1984 | Fixel | 129/92 BB |
| 4,621,629 | August 1985 | Koeneman | 128/92 YS |
| 4,612,920 | September 1986 | Lower | 128/92 BA |
| 4,617,922 | October 1986 | Griggs | 128/92 YS |
| 4,657,001 | April 1987 | Fixel | 128/92 YS |
| 5,041,116 | August 1991 | Wilson | 606/65 |
| 5,167,663 | December 1992 | Brumfield | 606/64 |
| 5,324,292 | June 1994 | Meyers | 606/73 |
| 5,454,813 | October 1995 | Lawes | 606/62 |
| 5,032,125 | July 1999 | Durham | 606/62 |
| 6,443,954 B1 | September 2002 | Bramlet et al. | 606/62 |
| 6,645,209 B2 | November 2003 | Hall, IV et al. | 606/69 |

ADDITIONAL REFERENCES

1. Cole, P. A. and Bhandari, M. "Specialty Update: What's new in Orthopaedic Trauma". J Bone Joint Surg 87A (12), 2005; 2823-2838.
2. Shaw, J. A. and Wilson, S. "Internal Fixation of Proximal Femur Fractures: A Biomechanical Comparison of the Gamma Locking Nail and the Omega Compression Hip Screw". Orthopedic Review 22 (1), 1993; 61-68.

DESCRIPTION

BACKGROUND OF THE INVENTION

The compression hip screw (also referred to as a dynamic hip screw or sliding hip screw) is a commonly used fracture fixation device for femoral neck and intertrochanteric fractures of the proximal femur. A variety of similar devices are available from multiple orthopaedic device manufacturers. A generic compression (dynamic, sliding) hip screw (FIG. 1) consists of three basic components: a lag screw which is screwed into the femoral head to secure the proximal fracture fragment; a side plate containing a hollow cylindrical portion for sliding interdigitation with the lag screw and an integrally attached bone plate for screw fixation to the femoral diaphysis; and a compressing screw which may be threaded into the lateral end of the lag screw and tightened against the side plate to draw the lag screw laterally within the cylindrical portion of the side plate.

The utility of the compression hip screw for fixation of the most common femoral neck and intertrochanteric hip fractures, with fracture planes relatively perpendicular to the anatomical axis of the femoral neck (and of the corresponding axis of insertion of the lag screw portion of the compression hip screw fixation device), is well documented. The ability of the lag screw portion of the fixation device to slide within the mating cylindrical portion of the fixation device side plate allows the fracture site to compress into a stable configuration when weight is applied to the femoral head or, alternatively, when the compressing screw is tightened. When tightened, the compressing screw pulls the lag screw (and attached proximal fracture fragment) laterally and, in the process, compresses the proximal (medial) and distal (lateral) fracture fragments. This is desirable, as a forcefully compressed interdigitation of irregular fracture fragments produces a stable fixation configuration.

The utility of the generic compression hip screw falls short when the fracture plane is relatively parallel to the femoral neck and corresponding axis of insertion of the lag screw portion of the fixation device. This fracture configuration is commonly referred to as a "reverse obliquity fracture." If the prototypical hip screw is used for fixation of a reverse obliquity facture, loss of reduction with lateral displacement of the proximal fragment is a frequent sequela. The forces of bearing weight, or even resting muscle tone, produce a shear force along the plane of the reverse obliquity fracture causing the proximal fracture fragment(s) to shift laterally relative to the distal diaphysial fragment. There is no design feature in the typical compression hip screw to stop this translation. In fact, the entire purpose of the compression hip screw, as currently configured, is to allow sliding translation.

Current recommendations for fixation of reverse obliquity fractures include low angle fixed blade plates, intramedulary fixation devices and external fixation hardware. Although each of these methods has its advocates, the relative ease and familiarity of use of the generic compression hip screw leads many orthopaedic surgeons to select this fixation methodology, where other choices may be more appropriate from a biomechanical perspective. This, and other factors related to alternative fixation methodology complications (Shaw et al.), lead Cole and Bhandari to decry, in a recently published update on orthopaedic trauma (Cole et al.), " . . . what is blatantly missing from contemporary locking plate inventories: an effective locking fixator for the proximal femur."

The optional locking capacity of the described Locking Compression Hip Screw extends the spectrum of fixation capabilities of the generic compression hip screw. When locked, the lag screw cannot slide within the mating side plate and, hence, will block lateral translation of the proximal fracture fragment, which is securely anchored to the lag screw via the large cancerous bone threads on its medial aspect. Once the hardware is locked, the reverse obliquity fracture (or high subtrochanteric fracture) can be compressed by releasing limb traction, attaching a routine compressing apparatus to the femur and side plate and/or utilizing the compression capability of the offset screw holes built into the side plates of most compression hip screw systems.

BRIEF DESCRIPTION OF PRIOR ART

Prior art describes multiple methods of preventing rotation of the lag screw within the cylindrical portion of the side plate of the generic compression hip screw. This is accomplished through a variety of mating flats, or key-ways on the lag screw and within the cylindrical portion of the side plate. Examples of prior art describing rotational blocks are: U.S. Pat. No. 4,432,358 (Fixel), U.S. Pat. No. 4,621,629 (Koeneman), U.S. Pat. No. 4,612,920 (Lower), U.S. Pat No. 4,617,922 (Griggs), U.S. Pat. No. 4,657,001 (Fixel), U.S. Pat. No. 5,324,292 (Meyers) and U.S. Pat. No. 6,645,209 B2 (Hall IV, et al.).

The Locking Compression Hip Screw may be manufactured with or without rotational blocks, in accordance with manufacturer preference and current patent holdings. The presence or absence of rotational blocks has no bearing on the proposed sliding lock modification offered in this patent application. As a rule, the presence of rotational blocks provides no clinical advantage, with the possible exception of the high femoral neck fracture (subcapital hip fracture), in that an interdigitated fracture has intrinsic stability to rotational displacement and the rotational stability offered by the lag screw, itself, is minimal.

U.S. Pat. No. 5,041,116 (Wilson) describes a sliding lock, consisting of a setscrew placed obliquity through the side plate, impinging on the head of the compressing screw. The position of the setscrew within the narrow side plate necessitates a setscrew of small diameter and limited structural integrity. This mechanism of locking has not been incorporated into the design of any manufactured compression hip screw and is distinctly different in design and method of achieving a lock between the lag screw and side plate from that presented in this application.

Multiple patents describe intramedullary fixation devices for proximal femur fracture fixation, most of which include a locking setscrew within the intramedullary rod, which impinges on the lag screw-like portion of the device. The fracture fixation system, itself, as well as the locking mechanism utilized, are distinctly different from that described in this application. Examples of this art are: U.S. Pat. No. 5,167,663 (Brumfield), U.S. Pat. No. 5,454,813 (Lawes), U.S. Pat. No. 5,032,125 (Durham) and U.S. Pat. No. 6,443,954 B1 (Bramlet et al.).

BRIEF SUMMARY OF THE INVENTION

With reverse obliquity fractures, the sliding feature of the generic compression hip screw is a decided disadvantage and may result in a shearing displacement of the major fracture fragments. The Locking Compression Hip Screw introduces the ability to prevent sliding motion of the lag screw within the cylindrical portion of the side plate. This is accomplished by modifying the generic side plate to include female threads within the lateral aspect of the cylindrical section and adding a mating threaded locking plug to the system, which may be screwed into the side plate until it abuts against the lateral end of the recessed lag screw. The compressing screw may then be inserted, in a co-axial fashion, through the central hole in the locking plug and screwed into the end of the lag screw, as describe previously. When tightened, the compression screw will pull the lag screw tightly against the locking plug, preventing sliding translation of the lag screw in either direction. This mode of use creates a locked relationship between the lag screw and side plate.

DETAILED DESCRIPTION OF INVENTION

Figure 1:
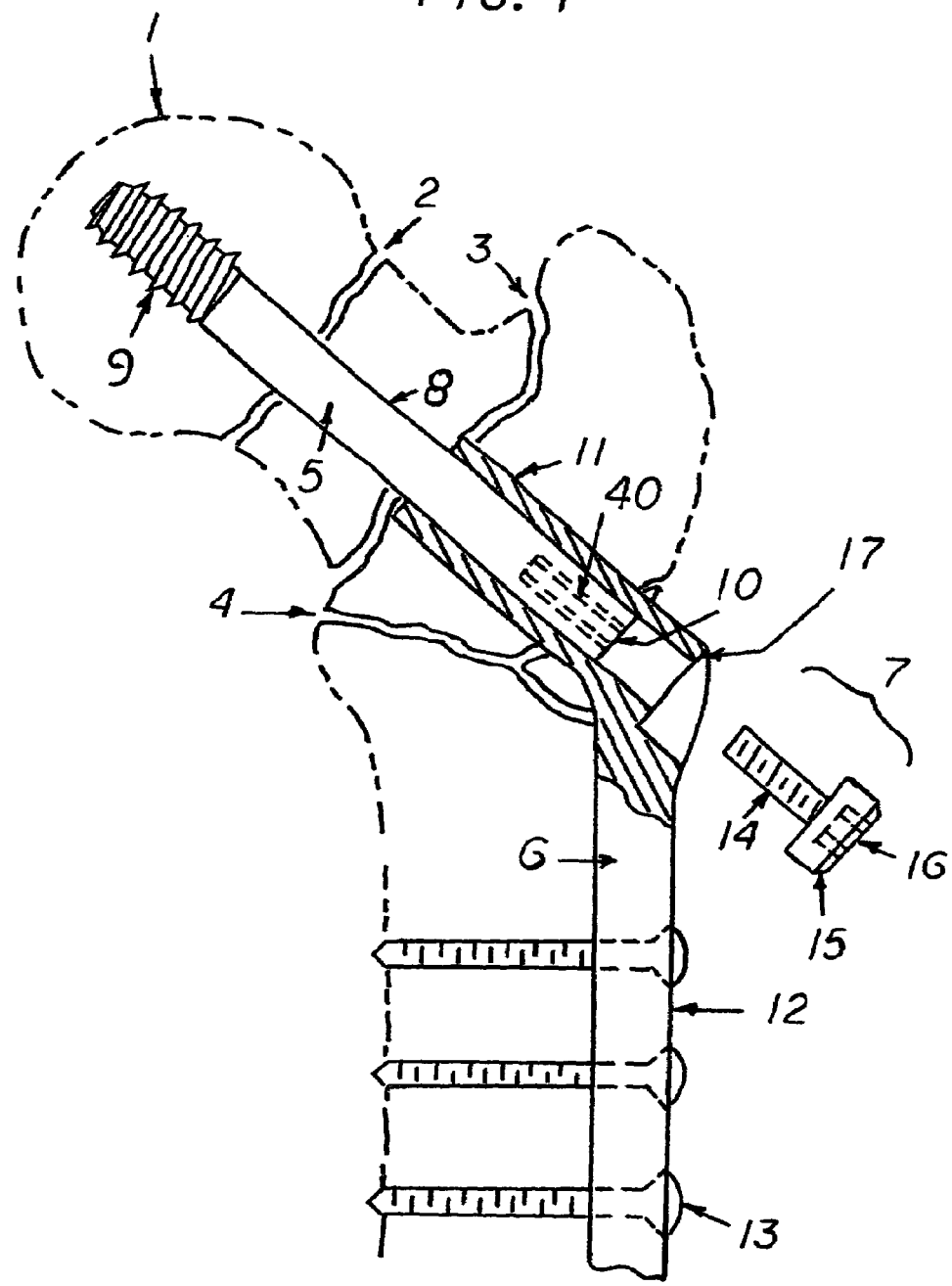
FIG. 1 shows a generic compression hip screw (prior art) within a schematic representation of the proximal femur.

FIG. 1 shows a generic compression hip screw within a schematic representation of the proximal femur 1. Fracture patterns well controlled by a conventional hip screw include the femoral neck fracture 2, and the intertrochanteric hip fracture 3. The reverse obliquity hip fracture 4 is not well stabilized with a conventional compression hip screw and it is towards this fracture pattern, with or without comminuted extensions, that the Locking Compression Hip Screw is directed.

The three integral parts of a generic compression hip screw are: the femoral head lag screw 5, the side plate 6, and the compressing screw 7.

The femoral head lag screw consists of a smooth metallic shank 8 of variable length, with course cancerous bone threads 9 on the medial end and axially aligned female threads within the lateral end 10. The lateral end 10 may also have a flat or slot milled on its surface so that a custom insertion tool (wrench) can gain torsional purchase on the lateral end, allowing the lag screw to be screwed into a previously reamed (and tapped) hole in the femoral neck and head. This detail is not shown, as it is not integral to the patent modification depicted in this application.

The side plate consists of a hollow cylindrical portion 11 (shown in cross section) for sliding interdigitation with the lag screw 5 and an integrally attached bone plate portion 12, which is designed for screw 13 fixation to the diaphysis of the proximal femur. During fracture fixation, the side plate 6 is slid over the previously inserted lag screw 5 and secured to the femur with bone screws 13. The cylindrical portion 11 is generally manufactured in different lengths to accommodate different fracture patterns and different sized bones. Similarly, the plate portion 12 may be fabricated in different lengths with a variable number and location of screw holes to accommodate different sized bones and different fracture patterns. Additionally, side plates 6 are generally fabricated with variable angular relationships between the cylindrical 11 and plate 12 portions to accommodate different anatomical neck-shaft angles.

The compressing screw 7 contains a threaded shank 14 and head 15. The male threads are matched to the female threads 40 within the lateral end 10 of the lag screw 5. The head 15 contains a recessed socket 16 for insertion of an Allen wrench or other screwdriver-like tool. When tightened into the lag 5 screw, the head 15 of the compressing screw 7 eventually seats on a countersunk flat 17 on the side plate 6. Further tightening draws the lag screw 5 laterally within the cylindrical portion 11 of the side plate 6. If the fracture plane is roughly perpendicular to the lag screw 5, this tightening action compresses the fracture site.

Figure 2:
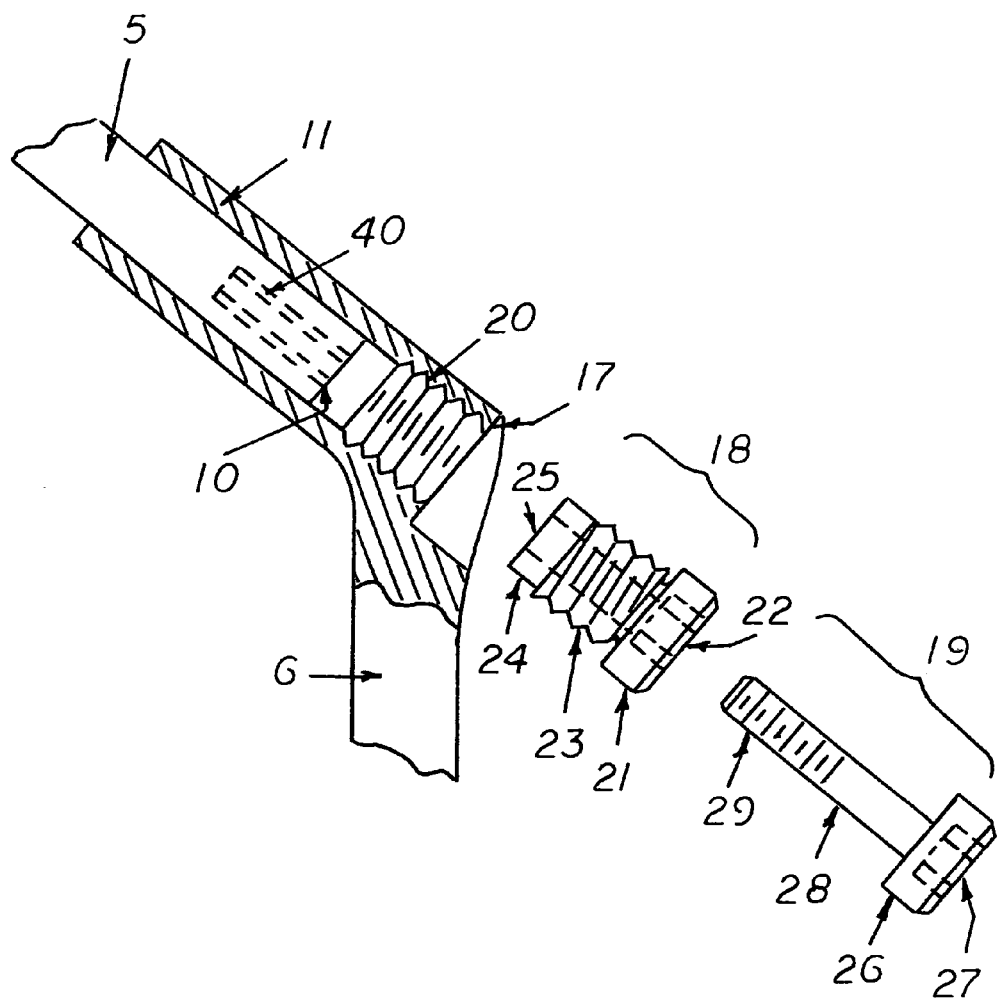
FIG. 2 shows the preferred embodiment of the Locking Compression Hip Screw, with a coned down view of the locking mechanism.
Figure 3:
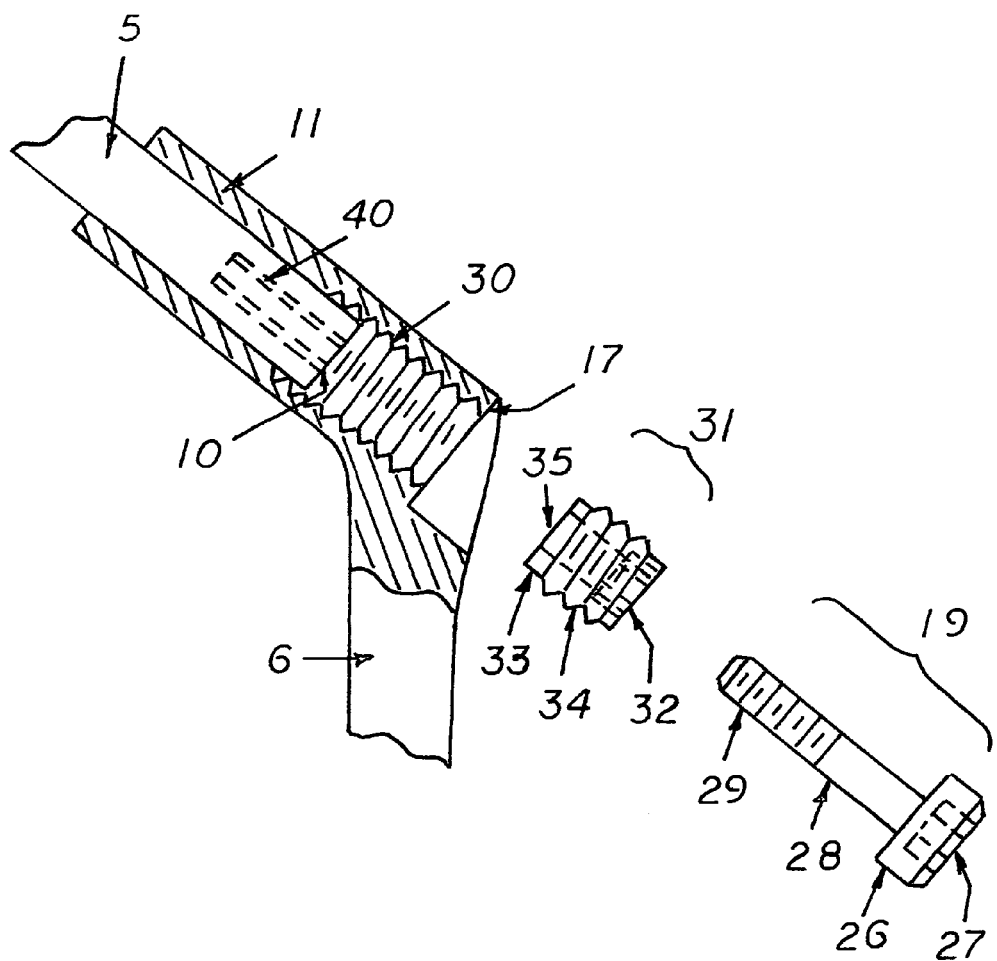
FIG. 3 shows an alternative embodiment of the Locking Compression Hip Screw, with a coned down view of the locking mechanism.

FIG. 2 shows the preferred embodiment of the Locking Compression Hip Screw locking mechanism. The side plate 6 is similar in design to a conventional side plate in most respects. Like most designs, it contains a cylindrical proximal portion 11 for sliding interdigitation with the femoral head lag screw 5. This cylindrical portion 11 may be fabricated in varying lengths to accommodate different fracture configurations and bone sizes. Its internal cross sectional dimension matches the shank 8 of the lag screw 5 and may contain a key-way, or similar mechanism, for rotational control of the lag screw 5 within the side plate 6. As depicted in FIG. 1, the cylindrical portion 11 is integrally attached to a bone plate (cut off in this figure), designed for screw fixation to the lateral aspect of the proximal femur diaphysis. The bone plate may be fabricated in different lengths to accommodate more or fewer screw holes and different fracture configurations. Additionally, the angle between the plate portion 12 and the cylindrical portion 11 may vary to accommodate different anatomical bone configurations. The side plate 6 also contains a countersunk flat 17, or alternatively shaped recess, at the base of the cylindrical portion 11 onto which the head 21 of the locking plug 18 rests in the preferred embodiment or, alternatively, the head 26 of the compressing screw 19 rests in the alternative embodiment (FIG. 3).

The unique feature of the Locking Compression Hip Screw side plate 6 is that the lateral end (base) of the cylindrical portion 11 contains a threaded section 20 for insertion of the locking plug 18. Female threads are machined or tapped into the base of the cylindrical portion 11 of sufficient length to accommodate the male threads 23 on the locking plug 18 without thread interference prior to fully seating the plug 18. The threads are schematically depicted as being of course dimension, but would, in reality, be of conventional machine screw size so as to remove little metallic stock from the junction between the cylindrical portion 11 and the plate portion 12 of the side plate 8. The thread configuration may be of Spiralock® (or similar) design, so as to prevent vibratory loosening of the locking plug 18, once inserted.

The locking plug 18 is of similar configuration to a conventional machine screw. It contains a head 21 on one end, with a recessed socket 22 for insertion of an Allen wrench or other screwdriver-like device. The central section contains male threads 23 of mating character and dimension to the female threads within the side plate 6. The end opposite the head 24 is cylindrical in shape with an outside diameter matching that of the shank 8 of the lag screw 5 and allowing a sliding fit within the cylindrical portion 11 of the side plate 6. This portion of the locking plug 18 would be manufactured in varying lengths so that a plug of appropriate length could be selected to fill the gap remaining between the lateral end 10 of the lag screw 5 and the threaded portion 20 of the side plate 6 at completion of fracture reduction. Spiralock® (or similar) thread design may be used to prevent loosening of the locking plug 18, once inserted. Alternatively, the undersurface of the head 21 may be serrated, tapered or incorporate a locking washer of standard design to provide augmented resistance to loosening when the locking plug 18 is tightened against the side plate 6.

The locking plug 18 contains a centrally reamed hole 25 throughout its entire length. This hole 25 is of appropriate diameter to allow a sliding passage of the compressing screw 19. The compressing screw 19 is of variable length and contains a head 26 with a recessed socket 27 for insertion of an Allen wrench or other screwdriver-like device. The shank 28 of the screw 19 is threaded 29 on the end opposite the head. The shank diameter is appropriate to allow a sliding fit within the locking plug 18 and of sufficient length to be inserted through the locking plug 18 and fully engage the female threads 40 of the lag screw 5. The male threads 29 of the compressing screw 19 are of a size and character to mate with the female threads 40 within the lateral end 10 of the lag screw 5. The thread configuration may be of Spiralock® (or similar) design to limit the potential for loosening of the compressing screw 19, once engaged with the lag screw 5 and fully tightened. Alternatively, the undersurface of the head 26 may be serrated, tapered or incorporate a locking washer of conventional design. When fully engaged in the lag screw 5, the head 26 of the compressing screw 19 will seat against the head of the locking plug 18 in a stacked fashion. Further tightening of the compressing screw 19 will draw the end lateral end 10 of the lag screw 5 tightly against the locking plug 18 and prevent sliding translation of the lag screw 5 in either direction.

FIG. 3 shows an alternative embodiment of the Locking Compression Hip Screw locking mechanism. In this embodiment, the female threads 30 within the cylindrical portion 11 of the side plate 6 are extended further up the cylinder so as to overlap the lateral end of the lag screw 5 at completion of the fracture reduction. The thread design may be of Spiralock® (or similar) configuration to prevent loosening of the locking plug 31, once inserted.

The alternative locking plug 31 is manufactured along the lines of a setscrew, which can be screwed completely into the side plate 6 until it contacts the lateral end 10 of the lag screw 5. One end of the locking plug 31 would contain a recessed socket 32 to accommodate an Allen wrench or other screwdriver-like tool used for insertion. The opposite end 33 would have a flat face for abutment against the lag screw 5. The male threads 34 covering the body of the alternative locking plug 31 would match the female threads 30 within the cylindrical portion 11 of the side plate 6 and may be of Spiralock® (or similar) configuration to help prevent loosening or backing out of the plug 31, once inserted. The center of the plug 31 contains an axially reamed hole 35, throughout its length, of sufficient diameter to allow sliding passage of the compressing screw 19.

The compressing screw 19 in this embodiment is of similar design to that described for the preferred embodiment. The screw head 26 would contain a recessed socket 27 to accommodate an Allen wrench or other screwdriver-like tool. The undersurface of the head 26 may be serrated, tapered, or incorporate a locking washer of conventional design to prevent loosening when tightened against the side plate 6. The threaded portion 29 and shank 28 would be of variable length and appropriate diameter to pass through the hole 35 in the locking plug 31 with a sliding fit. The male threads 29 on the compressing screw 19 would be matched to engage the female threads 40 of the lag screw 5 and may be of Spiralock® (or similar) configuration to prevent loosening, once tightened. When the compressing screw 19 is fully threaded into the lag screw 5, the head 26 of the compressing screw 19 will rest against the countersunk flat 17 on the side plate 6. Further tightening of the compressing screw 19 will pull the lag screw 5 tightly against the previously inserted locking plug 31, preventing sliding translation in either direction.

In view of the wide variety of embodiments to which the principles of the invention can be applied, the depicted embodiments should be considered as illustrative only, and not limiting the scope of this invention. The claimed invention includes all modifications that may be made by those skilled in the art.

What is claimed is:

1. A compression hip screw device, comprising:
   a lag screw having a smooth shank with a distal end and a proximal end, said distal end having coarse cancellous bone threads and said proximal end having an axially threaded hole, said proximal end having an outer diameter;
   a side plate having a hollow cylindrical portion and an integrally attached plate portion, said cylindrical portion having a distal aspect and a proximal aspect, said proximal aspect having an internally threaded section;
   a compressing screw having a distal end and a proximal end, said distal end having a threaded section;
   a locking plug consisting of a distal section, a middle section, and a proximal section; said locking plug having a hollow central core defined by a longitudinal axis extending through said distal section, said middle section, and said proximal section; said distal section having a free distal end and a proximal end that abuts said middle section at a distal end of said middle section, said middle section having a proximal end that abuts said proximal section at a distal end of said proximal section, said proximal section having a free proximal end; said distal section having no external threads and being cylindrical in shape, said distal section having a cross-section defined by a plane perpendicular to said longitudinal axis and a length extending parallel to said longitudinal axis from said free distal end to said proximal end of said distal section, said cross-section being constant over said length of said distal section, said cross section having a diameter equal to said outer diameter of said shank of said lag screw; said middle section having external threads dimensioned to mate with said internally threaded section of said cylindrical portion of said side plate; said proximal section having a recessed socket and no external threads;

wherein said lag screw is adapted for insertion into the femoral neck and head during the course of fracture fixation;

wherein said lag screw slidingly interdigitates with said cylindrical portion of said side plate;

wherein said integrally attached plate portion of said side plate is adapted for screw fixation to the lateral femoral diaphysis;

wherein said free distal end of said locking plug abuts against said proximal end of said lag screw to prevent lateral sliding translation of said lag screw within said cylindrical portion; and wherein said compressing screw is inserted through said central core of said locking plug, threaded into said axially threaded hole of said lag screw, and tightened against said locking plug or said side plate such that said compressing screw pulls said lag screw tightly against said locking plug to prevent sliding translation of said lag screw in either direction.

* * * * *